United States Patent

[19]

Hotta et al.

[11] Patent Number: 6,040,326
[45] Date of Patent: Mar. 21, 2000

[54] 3-DEOXYGLUCOSONE PRODUCTION INHIBITOR

[75] Inventors: Nigishi Hotta, Aichi; Hiroki Fujisawa, Hyogo, both of Japan

[73] Assignee: Nippon Zoki Pharmaceuticals Co., Ltd., Osaka, Japan

[21] Appl. No.: 08/997,872

[22] Filed: Dec. 24, 1997

[30] Foreign Application Priority Data

Dec. 27, 1996 [JP] Japan .................................. 8-357874

[51] Int. Cl.⁷ ................................................ A61K 31/415
[52] U.S. Cl. ......................... 514/386; 514/824; 514/390
[58] Field of Search ................................. 514/390, 824, 514/386

[56] References Cited

U.S. PATENT DOCUMENTS

| | | |
|---|---|---|
| Re. 32,919 | 5/1989 | Sarnoff . |
| 4,096,130 | 6/1978 | Kraft et al. . |
| 4,647,574 | 3/1987 | Ienaga et al. . |
| 4,656,034 | 4/1987 | Sarnoff . |
| 4,658,830 | 4/1987 | Sarnoff . |
| 4,661,469 | 4/1987 | Sarnoff . |
| 4,683,240 | 7/1987 | Ienaga et al. . |
| 4,772,585 | 9/1988 | Sarnoff et al. . |
| 4,832,682 | 5/1989 | Sarnoff . |
| 4,985,453 | 1/1991 | Ishii et al. . |
| 5,002,930 | 3/1991 | Sarnoff et al. . |
| 5,078,680 | 1/1992 | Sarnoff . |
| 5,084,473 | 1/1992 | Mikami et al. . |
| 5,681,843 | 10/1997 | Kotani et al. . |

FOREIGN PATENT DOCUMENTS

| | | |
|---|---|---|
| 0160 618 A1 | 11/1985 | European Pat. Off. . |
| 0194 226 A1 | 9/1986 | European Pat. Off. . |
| 0 353 198 A1 | 1/1990 | European Pat. Off. . |
| 0412940 A2 | 2/1991 | European Pat. Off. . |
| 0 718 289 A1 | 6/1996 | European Pat. Off. . |
| 0 718 290 A1 | 6/1996 | European Pat. Off. . |
| 26 12 926 A1 | 10/1977 | Germany . |
| 61-122275 | 6/1986 | Japan . |
| 62-14 | 1/1987 | Japan . |
| 63-166870 | 7/1988 | Japan . |
| 2019363 | 1/1990 | Japan . |
| 2225485 | 9/1990 | Japan . |
| WO 86/01110 | 2/1986 | WIPO . |
| WO 89/02890 | 4/1989 | WIPO . |

OTHER PUBLICATIONS

Patton, *J. Org. Chem..*, 32, No. 2, pp. 383–388 (1967).
Yonezawa, et al., *Nippon Kagaki Zasshi*, 89, No. 8, pp. 62–64 (1968).

"Pathologic Biochemistry and Clinics of Free Radicals, Inflammation and Antiinflammation", *Nippon Rinsho*, vol. 46, No. 10, pp. 93–97 (1988).
Ogawva, et al., "Syntheses of substituted 2,4–dioxo–thienopyrimidine–1–acetic acid and their evaluation as aldose reductase inhibitor", *European Journal Of Medicinal Chamistrychimica Theraputica*, vol. 28, No. 10, 1993, pp. 769–782.
Kanazu, et al., "Aldehyde reductase is a major protein associated with 3–deoxyglucosone reductase activity in rat, pig and human livers", *Biochem J.*, 279, 903–906 (1991).
Flynn, "Aldehyde Reductases: Monomeric Nadph–Dependent Oxidoreductases With Multfunctional Potential", *Biochem. Pharmacol.*, vol. 31 No. 17, 2705–2712 (1982).
Morrison and Boyd, *Organic Chemistry*, Allyn and Bacon, Inc., Boston (1965), pp. 806, 808, 847–848.
Malamas, "Quinazolineacetic Acid and Related Anaslogs as Aldose Reductase Inhibitors" J. Med. Chem. (1990), 34,(4), 1492–503, abstract.
CA60:532c, abstract.
Gangier, "Reactivity of Nucleophilic Uracil Derivatives" *J. Heterocycl. Chem.* (1994), 31, (6), 1707–14, abstract.

*Primary Examiner*—Keith D. MacMillan
*Attorney, Agent, or Firm*—Hollander Law Firm, P.L.C.

[57] ABSTRACT

The production of 3-deoxyglucosone, which is an intermediate in the Maillard reaction and induces a crosslinking glycation of proteins participating in various diseases, is inhibited with an inhibitor containing at least one parabanic acid derivative as an effective ingredient. The at least one parabanic acid derivative is represented by the following formula (I) or a pharmaceutically acceptable salt thereof:

$$X-N\underset{\underset{O}{\|}}{\overset{\overset{O}{\|}}{C}}N-(CH_2)_n-COOR \quad (I)$$

wherein, R is hydrogen or lower alkyl; X is hydrogen, alkyl, cycloalkyl, lower alkylcycloalkyl, phenyl or phenylalkyl which is optionally substituted with lower alkyl, lower alkoxy, nitro and/or halogen; and n is an integer of from 1 to 4. Inhibiting the production of 3-DG, which is a highly active intermediate which participates in the formation of crosslinked protein in the Maillard reaction is useful for the treatment and the prevention of various diseases induced by deposition into tissues or sclerosis or denaturation of crosslinked protein, or diseases induced by aging and diabetic complications.

12 Claims, 1 Drawing Sheet

3-DEOXYGLUCOSONE PRODUCTION INHIBITOR

FIELD OF THE INVENTION

The present invention relates to an inhibitor for the production of 3-deoxyglucosone which is an intermediate in the Maillard reaction, especially in its advanced stage (advanced glycosylation or secondary glycosylation).

BACKGROUND OF THE INVENTION

The Maillard reaction was reported for the first time in 1912 by Maillard who was a French biochemist. It is a nonenzymatic glycosylation (glycation) reaction which takes place between a reducing sugar, such as glucose, and an amino acid or protein. The reaction participates in browning, production of fragrant components, generation of good taste, denaturization of protein, etc. during heating or storage of food. Accordingly, the Maillard reaction has been mostly investigated by food chemists. In 1968, glycosylated hemoglobin (HbA1c), which is a small component of hemoglobin, was identified in the living body and was found to increase in diabetic patients. With this discovery, public attention has been drawn to the significance of the Maillard reaction in the living body. Its relation to the occurrence of adult diseases such as complications from diabetes and arteriosclerosis, and the progress of aging have been subjects of public interest.

Brownlee, M., et al., Science, Vol. 232, pp. 1629–1632 (1986) reported in 1986 concerning the Maillard reaction in a living body. The Maillard reaction can be divided into an early stage and an advanced stage. In the early stage an amino group of a protein and an aldehyde group of a reducing sugar form a Schiff's base, and then a stable product by an Amadori arrangement is produced via 1,2-enaminol. In the advanced stage, the above product is subjected to a long term reaction which produces advanced glycation endproducts (AGE) of the Maillard reaction characterized by fluorescence, browning and molecular crosslinking. This glycosylated product in the advanced stage produced by a crosslinking glycation of proteins has a lower solubility and is sclerosed whereby it is hardly metabolized by protease. As a result, the glycosylated product induces deposition into tissues or sclerosis, or denaturation of proteins which is a cause of the onset of various diseases.

There are many kinds of proteins which are crosslinked by means of the Maillard reaction in vivo. Proteins having slow metabolic turnover (such as collagen, elastin, hemoglobin, erythrocyte membrane, myelin, tubulin, LDL, fibrin, serum albumin, lens protein and renal glomerular basement membrane) are particularly apt to be polymerized in a crosslinking manner. With regard to a crosslinking reaction of protein by the Maillard reaction, the above-mentioned proteins having slow metabolic turnover are affected even if the blood sugar level is normal whereby aging and deterioration of the proteins are induced.

It is believed that such aging and deterioration of protein by the crosslinking glycation are important causes of the onset of various diseases such as adult diseases where the frequency of the onset increases with aging. Accordingly, if production of crosslinked protein (a glycated product in the advanced stage) is retarded or is substantially suppressed by a drug, the drug may be used for treatment or prevention of diseases accompanied by aging or those induced by deposition into tissues or sclerosis or denaturation of crosslinked protein. Such a drug may also be used to lengthen an animal's life span.

It has been known that an intermediate (3-deoxyosone) which is quite highly reactive with an amino group of proteins, etc. is produced from the above-mentioned 1,2-enaminol which is an intermediate in the Maillard reaction. 3-Deoxyosone corresponds to a mono-dehydrated substance of a reducing sugar and the substance which is produced from glucose or from fructose is 3-deoxyglucosone (3-DG). The substance which is believed to be most important in the production of AGE of the Maillard reaction is said 3-DG. Although various dicarbonyls are produced in the Maillard reaction, 3-DG is produced in the highest amount. As compared with glucose or the like, 3-DG is highly reactive with amino compounds and has a very high activity for resulting in a crosslinking of protein. The above-mentioned AGE is an index for the production of glycated protein. As a result of studies by many researchers, various candidate substances have been identified already. Among them, AGE compounds such as derivatives of imidazolone, pyrropyridine and pyralin are believed to be derived from 3-DG and it is becoming clear that 3-DG greatly participates in the formation of crosslinking in protein in vivo.

As mentioned above, production of a crosslinked protein induces aging and deterioration of protein existing in a living body is a factor which participates in the onset and worsening of various diseases. Therefore, substances which inhibit the Maillard reaction in vivo have been investigated. For example, Japanese Examined Patent Publication (JP) Hei-06/067,827 B. Publication (JP) Hei-06/067,827 A discloses inhibitors for the Maillard reaction which suppress the advanced stage glycosylation of a target protein by reaction with the carbonyl group of the early stage glycosylated product such as 3-DG. Although aminoguanidine which is mentioned as an effective component thereof is one of the substances which have been most extensively studied in this field, said compound has not been practically used as a pharmaceutical agent yet. In addition, thiosemicarbazides, 1,3-diaminoguanidine, benzoylhydrazine, etc. (JP Sho-64/056,614 A); carbazine derivatives (JP Hei-02/167,264 A); benzopyran derivatives (JP Hei-03/204,874 A); benzothiazole derivatives, benzimidazole derivatives, etc. (JP Hei-06/305,964 A); hydantoin derivatives (JP 06/135,968 A); imidazolidine derivatives (JP Hei-07/133,264 A); thiazolidines of a pyrazole type (JP Hei-08/157,473 A); etc. have been disclosed as useful Maillard reaction inhibitors.

In each of the above-mentioned patent publications, inhibitory activity towards the Maillard reaction was measured by means of the amount of crosslinkingly polymerized protein or AGE (intensity of fluorescence) produced, which is a final product of the Maillard reaction, as an index. However, the present inventors used the amount of 3-DG produced which is a most important and highly active intermediate in the crosslinking of protein in vivo as an index of inhibiting action towards the Maillard reaction. 3-DG is a causative substance participating in the crosslinking of proteins in a living body. Accordingly, drugs which inhibit the production of 3-DG are highly useful as excellent inhibitors for the production of crosslinked proteins.

The present invention provides novel inhibitors for the production of 3-deoxyglucosone (3-DG) which is an intermediate in the Maillard reaction and which induces a crosslinking glycation of proteins participating in various diseases.

SUMMARY OF THE INVENTION

The production of 3-deoxyglucosone (3-DG) and crosslinking of proteins by the Maillard reaction in vivo is inhibited by at least one parabanic acid derivative represented by the formula (I) or pharmaceutically acceptable salt thereof:

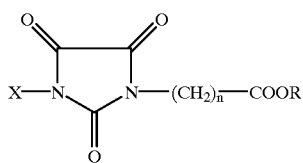

(I)

wherein,

R is hydrogen or lower alkyl;

X is hydrogen, alkyl, cycloalkyl, lower alkylcycloalkyl, phenyl or phenylalkyl which is optionally substituted with lower alkyl, lower alkoxy, nitro and/or halogen; and n is an integer of from 1 to 4.

Inhibiting the production of 3-deoxyglucosone may be used for the treatment or prevention of aging, a disease accompanied by aging or a disease induced by deposition into tissues or sclerosis or denaturization of crosslinked protein. The diseases treated in accordance with the present invention may be manifested in patients having normal blood sugar levels. For example, proteins having a slow metabolic turnover, such as collagen, elastin, hemoglobin, erythrocyte membrane, myelin, tubulin, LDL, fibrin, serum albumin, lens protein and renal glomerular basement membrane, may be crosslinked or polymerized even if the blood sugar level is normal. Thus, patients having a normal blood sugar level, but an abnormal level of 3-DG, may be treated with a parabanic acid derivative to reduce 3-DG levels and substantially retard or suppress production of crosslinked protein for the prevention or treatment of aging or diseases associated with aging. Diseases which may be treated or prevented in accordance with the method of the present invention include arteriosclerosis, arthrosclerosis, coronary artery or heart diseases, peripheral circulatory diseases, cerebrovascular diseases, atherosclerosis, senile cataract, cancer, and complications associated with diabetes mellitus, such as diabetic neuropathy, diabetic retinopathy, diabetic nephropathy, diabetic cataract, diabetic microvascular diseases, diabetic arteriosclerosis or diabetic skin diseases. For treating or preventing such diseases, the concentration of 3-deoxyglucosone in the plasma of a patient may be determined, and a pharmaceutically effective amount of a 3-deoxyglucosone inhibitor may be administered to substantially reduce or suppress production of 3-DG to normal levels.

DETAILED DESCRIPTION OF THE INVENTION

Figure 1:
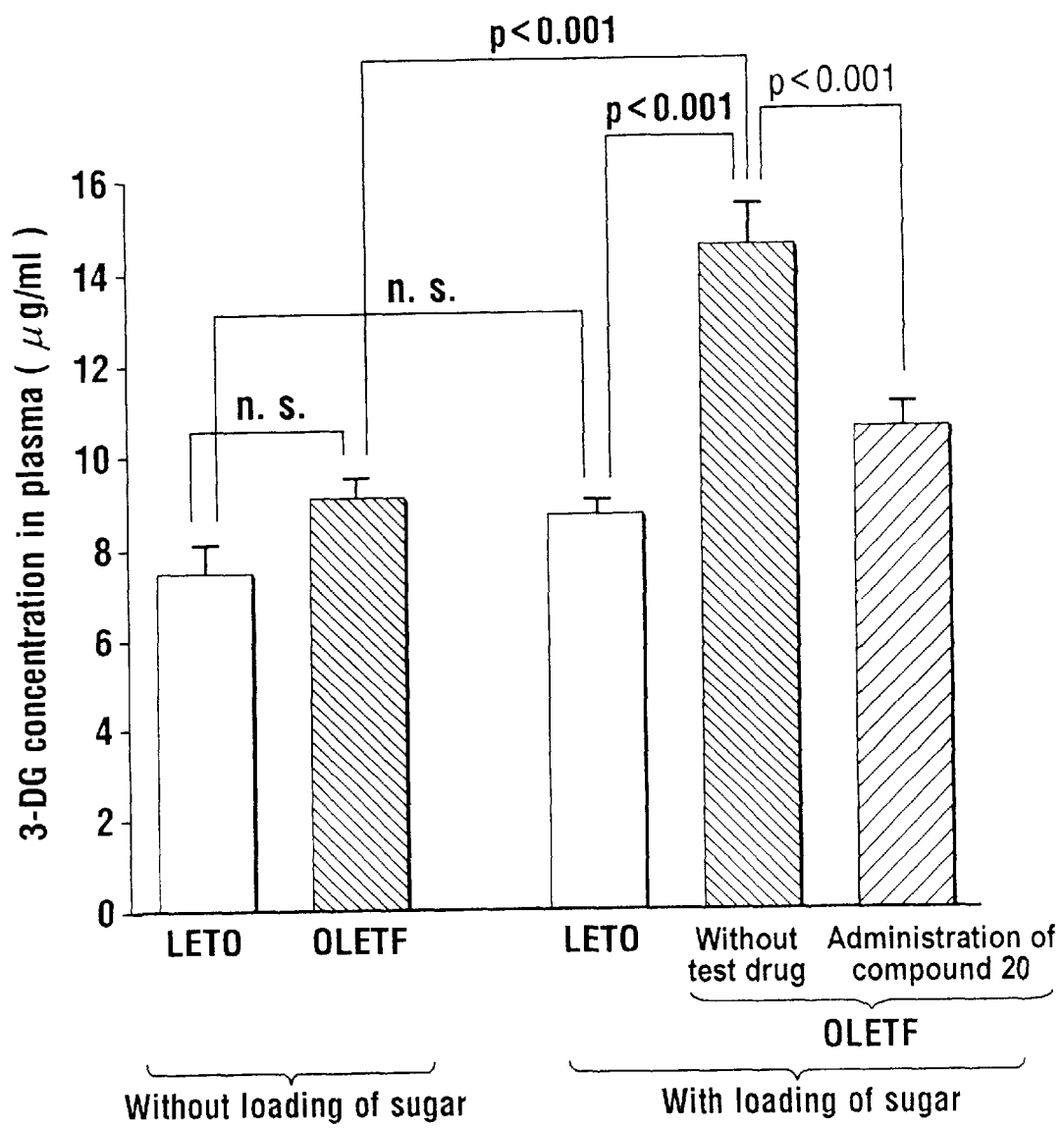
FIG. 1 shows the inhibitory activity of the present compounds on 3-DG production.

The present invention provides a method for inhibiting the production of 3-deoxyglucosone for the treatment or prevention of aging, a disease accompanied by aging or induced by deposition into tissues or sclerosis or denaturization of crosslinked protein. In embodiments of the invention, the concentration of 3-deoxyglucosone in the plasma of a patient may be determined and then a patient in need of said treatment or prevention may be administered a pharmaceutically effective amount of a 3-deoxyglucosone inhibitor containing at least one parabanic acid derivative.

The inhibitor for the production of 3-deoxyglucosone (3-DG) in accordance with the present invention contains at least one parabanic acid derivative represented by the following formula (I) or pharmaceutically acceptable salts thereof as an effective ingredient:

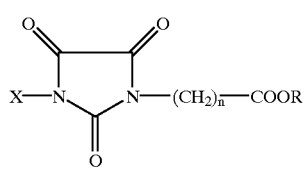

(I)

wherein R is hydrogen or lower alkyl; X is hydrogen, alkyl, cycloalkyl, lower alkylcycloalkyl, phenyl or phenylalkyl which is optionally substituted with lower alkyl, lower alkoxy, nitro and/or halogen; and n is an integer of from 1 to 4.

In the above-mentioned formula (I), where R is hydrogen or lower alkyl, preferred alkyl groups are a linear or branched alkyl having 1 to 4 carbon atoms such as methyl, ethyl, propyl, isopropyl, butyl, isobutyl, sec-butyl or tert-butyl.

In embodiments of the invention, X may be hydrogen, a linear or branched alkyl having 1 to 8 carbon atoms, such as methyl, ethyl, propyl, isopropyl, butyl, isobutyl, sec-butyl, tert-butyl, pentyl, isopentyl, neopentyl, tert-pentyl, hexyl, heptyl or octyl; cycloalkyl having 3 to 8 carbon atoms, such as cyclopropyl, cyclobutyl, cyclopentyl, cyclohexyl, cycloheptyl or cyclooctyl; lower alkylcycloalkyl, for example, said cycloalkyl having a linear or branched alkyl of 1 to 3 carbon atoms such as methyl, ethyl, propyl or isopropyl; phenyl or phenylalkyl, for example, alkyl of 1 to 6 carbon atoms bonded to phenyl, such as benzyl, phenylethyl, phenylpropyl, phenylbutyl, phenylpentyl or phenylhexyl, which may optionally have a linear or branched alkyl having 1 to 3 carbon atoms such as methyl, ethyl, propyl or isopropyl, a linear or branched alkoxy having 1 to 3 carbon atoms such as methoxy, ethoxy, propoxy or isopropoxy, nitro and/or halogen such as fluoro, chloro, bromo or iodo.

Preferred embodiments of a 3-deoxyglucosone (3-DG) production inhibitor containing the compound of the present invention represented by the above-given formula (I) are:

(1) A 3-Deoxyglucosone production inhibitor containing the compound represented by the above formula (I) wherein R is hydrogen.

(2) An agent according to the above-given paragraph (1) wherein n is 1.

(3) An agent according to the above-given paragraph (2) wherein X is phenylalkyl.

(4) An agent according to the above-given paragraph (3) wherein X is benzyl.

(5) An agent according to the above-given paragraph (4) wherein X is benzyl which is substituted with nitro.

(6) An agent according to the above-given paragraph (4) wherein X is benzyl which is substituted with halogen.

(7) An agent according to the above-given paragraph (4) wherein X is benzyl which is substituted with nitro and halogen.

The preferred compounds of the present invention are:
[Compound 1] 3-Carboxymethyl-1-methylparabanic acid
[Compound 2] 1-Butyl-3-carboxymethylparabanic acid
[Compound 3] 3-Carboxymethyl-1-isobutylparabanic acid
[Compound 4] 3-Carboxymethyl-1-hexylparabanic acid

[Compound 5] 3-Carboxymethyl-1-(4-methylcyclohexyl) parabanic acid
[Compound 6] 1-Benzyl-3-carboxymethylparabanic acid
[Compound 7] 3-Carboxymethyl-1-(2-methylbenzyl) parabanic acid
[Compound 8] 3-Carboxymethyl-1-(4-methylbenzyl) parabanic acid
[Compound 9] 3-Carboxymethyl-1-(2-methoxybenzyl) parabanic acid
[Compound 10] 3-Carboxymethyl-1-(3-methoxybenzyl) parabanic acid
[Compound 11] 3-Carboxymethyl-1-(3,4-dimethoxybenzyl) parabanic acid
[Compound 12] 3-Carboxymethyl-1-(2-chlorobenzyl) parabanic acid
[Compound 13] 3-Carboxymethyl-1-(3-chlorobenzyl) parabanic acid
[Compound 14] 3-Carboxymethyl-1-(4-chlorobenzyl) parabanic acid
[Compound 15] 1-(4-Bromobenzyl)-3-carboxymethylparabanic acid
[Compound 16] 3-Carboxymethyl-1-(4-fluorobenzyl) parabanic acid
[Compound 17] 3-Carboxymethyl-1-(2,4-dichlorobenzyl) parabanic acid
[Compound 18] 3-Carboxymethyl-1-(3,4-dichlorobenzyl) parabanic acid
[Compound 19] 3-Carboxymethyl-1-(2-nitrobenzyl) parabanic acid
[Compound 20] 3-Carboxymethyl-1-(3-nitrobenzyl) parabanic acid
[Compound 21] 3-Carboxymethyl-1-(4-nitrobenzyl) parabanic acid
[Compound 22] 3-Carboxymethyl-1-(4-chloro-3-nitrobenzyl)parabanic acid
[Compound 23] 3-Carboxymethyl-1-(2-pbenylethyl) parabanic acid
[Compound 24] 3-Carboxymethyl-1-(2-(4-methylphenyl) ethyl)parabanic acid
[Compound 25] 3-Carboxymethyl-1-(2-(3,4-dimethoxyphenyl)ethyl)parabanic acid
[Compound 26] 3-Carboxymethyl-1-(2-(2-chldorophenyl) ethyl)parabanic acid
[Compound 27] 1-(2-(4-Bromophenyl)ethyl)-3-carboxymethylparabanic acid
[Compound 28] 3-Carboxymethyl-1-(2-(3,4-dichlorophenyl)ethyl)parabanic acid
[Compound 29] 3-Carboxymethyl-1-(2-(3-nitrophenyl) ethyl)parabanic acid
[Compound 30] 3-Carboxymethyl-1-(3-phenylpropyl) parabanic acid
[Compound 31] 3-Carboxymethyl-1-(4-phenylbutyl) parabanic acid
[Compound 32] 3-Carboxypropyl-1-(3,4-dichlorobenzyl) parabanic acid
[Compound 33] 3-Carboxymethyl-1-phenylparabanic acid
[Compound 34] 1-Carboxymethylparabanic acid The parabanic acid derivatives of the present invention include pharmaceutically acceptable salts of the compounds represented by the above-given formula (I). Exemplary salts of the compounds of general formula (I) are salts of the compounds of formula (I) with an alkali metal such as sodium and potassium, salts with an alkaline-earth metal such as calcium and magnesium, salts with other metals such as aluminum, and salts with bases such as ammonia and organic amines. The parabanic acid derivatives of the present invention may also include their metal complexes, for example, complexes with zinc, nickel, cobalt, copper, iron, etc. These pharmaceutically acceptable salts and metal complexes can be produced, by conventional methods, from parabanic acid derivatives of the present invention in free form, by interchange with each other or by conversion from one to another.

When there are stereoisomers such as cis-trans isomers, optical isomers, and conformational isomers for the compounds of the present invention, or when the compounds exist as hydrates, the present invention includes any and all of them. The compounds of the present invention and the methods for manufacturing them are disclosed, for example, in Japanese patent publication no. JP Hei-02/040,368 A published Feb. 9, 1990 and its corresponding U.S. Pat. No. 4,985,453 to Ishii et al, both of which are incorporated by reference in their entireties.

The compounds of the present invention can be made into pharmaceutical compositions or preparations by combining one or more of the compounds with at least one pharmaceutical carrier or diluent. They can be made into various types of preparations by known methods. The pharmaceutical preparations or compositions may be made into solid, semi-solid, liquid or aerosol formulations for oral administration (e.g. tablets, capsules, powders, liquids, etc.) and for parenteral administration (e.g. for subcutaneous, intravenous, intramuscular, intrarectal and intranasal administrations). In preparing the pharmaceutical compositions or preparations, the compounds of the present invention may be used in the form of their pharmaceutically acceptable salts.

The compounds of the present invention may be used either solely or jointly in pharmaceutically effective amounts for treating animals or humans. They may also be used in pharmaceutically effective amounts in combination with pharmaceutically effective amounts of other pharmaceutically active components in pharmaceutical compositions or preparations.

In the case of preparations for oral administration, one or more of the compounds of the present invention alone or together with commonly-used pharmaceutically acceptable excipients in pharmaceutically acceptable amounts such as a suitable pharmaceutically acceptable additive or carrier (e.g. lactose, mannitol, corn starch, potato starch, etc.) may be mixed with one or more pharmaceutically acceptable: (1) binders such as crystalline cellulose, cellulose derivatives, gum arabicum, corn starch, gelatin, etc., (2) disintegrating agents such as corn starch, potato starch, potassium carboxymethyl-cellulose, etc., (3) lubricating agents such as talc, magnesium stearate, etc., and (4) other pharmaceutically acceptable excipients including pharmaceutically acceptable bulking agents, moisturizing agents, buffers, preservatives, perfuimes and the like to obtain tablets, diluted powders, granules or capsules.

Alternatively, suppositories may be prepared by mixing at least one compound of the present invention with pharmaceutically acceptable amounts of one or more pharmaceutically acceptable fatty/oily bases (e.g. cacao butter), emulsified bases, water-soluble bases (e.g. Macrogol), hydrophilic bases, etc.

In the case of parenteral administration using injections, for example, it is possible to prepare solutions or suspensions of one or more compounds of the present invention in pharmaceutically acceptable carriers such as aqueous and nonaqueous solvents such as distilled water for injection, physiological saline solution, Ringer's solution, plant oil, synthetic fatty acid glycerides, higher fatty acid esters, propylene glycol, etc.

In the case of inhalations or aerosol preparations, at least one compound of the present invention in the form of a liquid or minute powder can be filled up in an aerosol container with a gas or liquid spraying agent, and if desired, with conventional adjuvants such as one or more pharmaceutically acceptable humidifying agents or dispersing agents. They can also be used as pharmaceuticals for a non-pressurized preparation such as in a nebulizer or an atomizer.

In order to make the compounds of the present invention into collyriums, they can be prepared as a solution or suspension together with an aqueous solvent such as sterile, purified water and physiologically saline solution, or a non-aqueous solvent for injection. The collyriums may also include pharmaceutically acceptable preservants, sterilizing agents, pH adjusting agents, and the like.

It is also possible, depending upon the type of the disease, to prepare pharmaceutical preparations other than the above-mentioned ones such as ointments, poultices, etc.

The preferred dosage of the compound of the present invention varies depending upon the subject to be administered (age, body weight, symptoms, etc. of the patient), form of the preparation, method for the administration, term for the administration, etc. To achieve the desired result, the compound may be usually administered by the oral route with a daily dose of 10–3,000 mg, preferably 20–1,500 mg per day, to common adults.

In the case of parenteral administration such as by injection, the preferred dosage may be from one-third to one-tenth of the above-mentioned oral dosage because of the effects of absorption, etc. in the oral route.

The present invention is further illustrated by the following non-limiting examples wherein all parts, percentages and ratios are by weight, all temperatures are in ° C., and all reactions are conducted at about atmospheric pressure unless indicated to the contrary:

EXAMPLE 1

Parabanic acid derivatives of the present invention were subjected to pharmacological testing to demonstrate their inhibitory activity toward the production of 3-deoxyglucosone (3-DG):

(1) Method for Measuring 3-DG

Measurement of 3-DG was conducted in accordance with a method by Yamada et al. wherein 3-DG was reacted with 2,3-diaminonaphthalene to convert it to a derivative and its intensity of fluorescence was measured to determine 3-DG [J. Biol. Chem., vol. 269, no. 32, p. 20,275–20,280 (1994)]. Thus, 0.1 ml of 60% perchloric acid was added to 1 ml of plasma to remove protein. After being allowed to stand for one hour under cooling with ice, the mixture was centrifuged at 4° C. and 0.6 ml of the supernatant liquid was neutralized with 1 ml of a saturated aqueous solution of sodium bicarbonate. To the neutralized supernatant liquid were added 25 $\mu$l of a methanolic solution of 1 ppm of 3,4-hexanedione (an internal standard) and 0.1 ml of a 0.1% methanolic solution of 2,3-diaminonaphthalene (a reaction reagent). The mixture was reacted at 4° C. for one night. The reaction product was extracted with 4 ml of ethyl acetate, and the extract was concentrated and evaporated to dryness in an evaporator. The resulting residue was dissolved in a 50% aqueous solution of methanol and filtered through an Ultrafree C3-LG centrifugal filtering unit (manufactured by Millipore) to give a sample for the measurement.

For measurement of 3-DG in the samples, an HPLC column TSK-GEL, ODS-80Ts (manufactured by Tosoh; 4.6×150 mm) was used. As mobile phases, a buffer A (phosphate buffer:methanol:acetonitrile=7:2:1) and a buffer B (phosphate buffer: methanol:acetonitrile=4:3:3) were used. An elution was conducted at the column temperature of 40° C. and a flow rate of 1 ml/minute by exchanging with a linear gradient of 0–100% from the buffer A to the buffer B during 20–26 minutes. 50 $\mu$l of the sample were loaded into the column and 3-DG and the internal standard derivative were detected by means of fluorescence (Em. 503 nm, Ex. 271 nm). Quantitative determination was conducted by an internal standard method from the resulting peak areas. 3-DG concentrations in plasma of healthy persons and of patients suffering from diabetes were measured by this method whereupon it was found that the 3-DG concentration in plasma of diabetic patients was about two-fold the 3-DG concentration in plasma of healthy persons.

(2) Inhibitory Action of the Test Drug to 3-DG Production

In this test, OLETF (Otsuka Long-Evans Tokushima Fatty) rat which is a naturally-occurring model animal for diabetes mellitus was used [Byotai Seiri, vol. 33, no. 1, p. 21–16 (1994)]. It was reported that OLETF rats show significant hyperglycemia when loaded with sugar to result in an onset of diabetic neuropathy. As a normal control rat, LETO (Long-Evans Tokushima Otsuka) which is genetically related to the OLETF rat but does not give rise to diabetes at all was used.

OLETF rats of 20 weeks age and LETO rats which were the normal control thereof were classified into the following five groups. They were: 1) LETO control; 2) LETO loaded with sucrose; 3) OLETF control; 4) OLETF loaded with sucrose; and 5) OLETF loaded with sucrose and administered with the test drug. Loading with sugar was conducted by giving drinking water containing 30% sucrose. The test drug was incorporated into a solid feed at a concentration of 0.5% by weight and administered by mixing with said feed as such. After loading of sugar and administration of the test drug were conducted for five months, the concentration of 3-DG in plasma was measured. As a result of checking the amount of the feed taken by the rat, it was found that the dose of the test drug (Compound 20 of the present invention) per kg of body weight of the rat was about 50–80 mg/day. One example of the results is given in FIG. 1.

As shown in FIG. 1, in the case of normal LETO rats, 3-DG in plasma did not increase even when loaded with sugar. However, in the case of OLETF rats which are naturally-occurring model animals for diabetes, the 3-DG concentration in plasma significantly increased upon loading with sugar. Against said increase in 3-DG, a significant decrease in 3-DG was noted in the group where the compound of the present invention was administered.

It is clear from the results of the above pharmacological test that the compound of the present invention has an action of inhibiting the production of 3-DG which is a highly active intermediate and participates in crosslinked protein formation in the Maillard reaction. Therefore, the compound of the present invention is useful in the treatment and the prevention of various diseases induced by deposition into tissues or sclerosis or denaturation of crosslinked protein (such as arteriosclerosis, arthrosclerosis, coronary artery diseases, peripheral circulatory diseases and cerebrovascular diseases), similar diseases induced by aging (such as atherosclerosis, coronary artery heart diseases, cerebrovascular diseases, senile cataract and cancer) and diabetic complications (such as diabetic neuropathy, diabetic retinopathy, diabetic nephropathy, diabetic cataract, diabetic microvascular diseases, diabetic arteriosclerosis and diabetic skin diseases).

The parabanic acid derivatives may be used for the inhibition of the crosslinking of proteins by means of the Maillard reaction in vivo. The protein may be a slow metabolic turnover protein such as collagen, elastin, hemoglobin, erythrocyte membrane, myelin, tubulin, LDL, fibrin, serum albumin, lens protein and renal glomerular basement membrane. Proteins having slow metabolic turnover may be crosslinked or polymerized even if the blood sugar level is normal which may result in aging or deterioration of the proteins. Thus, patients having a normal blood sugar level but an abnormal level of 3-DG may be treated with a parabanic acid derivative to reduce 3-DG levels and substantially retard or suppress production of crosslinked protein for the prevention or treatment of aging or diseases associated with aging.

In Japanese patent publication no. JP Hei-02/040,368 A and corresponding U.S. Pat. No. 4,985,453 to Ishii et al, where the parabanic acid derivatives of the present invention are mentioned, it is disclosed that the compounds exhibit an inhibitory action to aldose reductase. With respect to the causes for the onset of diabetic complications, the elevation of activity of the polyol metabolic pathway and the glycation of protein have been known as main onset mechanisms. The compounds of the present invention not only suppress the glycation of protein due to inhibitory action to 3-DG production but also have an inhibitory action to aldose reductase participating in the exaggeration of activity of the polyol metabolic pathway. Accordingly, the compounds of the present invention are very highly useful as drugs, preferably for treatment or prevention of diabetic complications.

We claim:

1. A method for inhibiting the production of 3-deoxyglucosone for the treatment or prevention of effects of aging, a disease selected from atherosclerosis, coronary heart disease, cerebrovascular disease, senile cataract, or a disease induced by deposition into tissues or sclerosis or denaturization of crosslinked protein, or complications associated with diabetes mellitus comprising determining the concentration of 3-deoxyglucosone in the plasma of a patient and administering to a patient in need of such treatment or prevention a pharmaceutically effective amount of a 3-deoxyglucosone inhibitor containing at least one parabanic acid derivative represented by the formula (I) or pharmaceutically acceptable salt thereof:

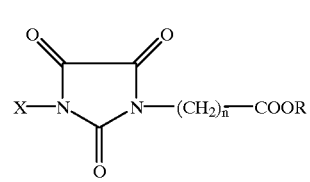

wherein

R is hydrogen or lower alkyl;

X is hydrogen, alkyl, cycloalkyl, lower alkylcycloalkyl, phenyl or phenylalkyl which is optionally substituted with lower alkyl, lower alkoxy, nitro and/or halogen; and n is an integer of from 1 to 4.

2. A method according to claim 1 wherein said at least one parabanic acid derivative is an inhibitor for the production of crosslinked protein.

3. A method as claimed in claim 1 wherein the 3-deoxyglucosone is inhibited for treatment or prevention of a disease induced by deposition into tissues and sclerosis or denaturation of crosslinked protein.

4. A method as claimed in claim 3 wherein said disease is arteriosclerosis, arthrosclerosis, a coronary artery disease, a peripheral circulatory disease or a cerebrovascular disease.

5. A method as claimed in claim 1 wherein 3-deoxyglucosone production is inhibited to prevent or to treat effects of aging.

6. A method as claimed in claim 1 wherein 3-deoxyglucosone production is inhibited to treat or to prevent atherosclerosis, coronary heart disease, cerebrovascular disease, or senile cataract.

7. A method as claimed in claim 1 wherein 3-deoxyglucosone production is inhibited to treat or prevent complications associated with diabetes mellitus.

8. A method as claimed in claim 7 wherein said 3-deoxyglucosone production is inhibited to treat or to prevent diabetic neuropathy, diabetic retinopathy, diabetic nephropathy, diabetic cataract, diabetic microvascular diseases, diabetic arteriosclerosis or diabetic skin diseases.

9. A method for the treatment of arteriosclerosis, arthrosclerosis, a coronary artery or heart disease, a peripheral circulatory disease, a cerebrovascular disease, atherosclerosis, or senile cataract comprising administering to a patient in need of said treatment a pharmaceutically effective amount of at least one parabanic acid derivative to substantially inhibit the production of 3-deoxyglucosone, said at least one parabanic acid derivative being represented by the formula (I) or pharmaceutically acceptable salt thereof:

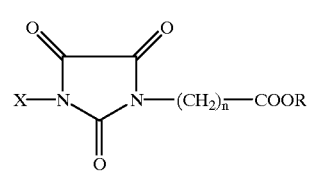

wherein,

R is hydrogen or lower alkyl;

X is hydrogen, alkyl, cycloalkyl, lower alkylcycloalkyl, phenyl or phenylalkyl which is optionally substituted with lower alkyl, lower alkoxy, nitro and/or halogen; and n is an integer of from 1 to 4.

10. A method for the inhibition of the crosslinking of proteins by means of the Maillard reaction in vivo comprising determining the concentration of 3-deoxyglucosone in the plasma of a patient and administering to a patient in need of said inhibition, pharmaceutically effective amount of at least one parabanic acid derivative to substantially inhibit the production of 3-deoxyglucosone, said at least one parabanic acid derivative being represented by the formula (I) or pharmaceutically acceptable salt thereof:

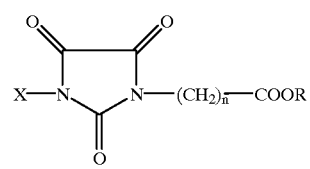 (I)

wherein,

R is hydrogen or lower alkyl;

X is hydrogen, alkyl, cycloalkyl, lower alkylcycloalkyl, phenyl or phenylalkyl which is optionally substituted with lower alkyl, lower alkoxy, nitro and/or halogen; and n is an integer of from 1 to 4.

11. A method as claimed in claim 10 wherein said protein is a slow metabolic turnover protein selected from the group consisting of collagen, elastin, hemoglobin, erythrocyte membrane, myelin, tubulin, LDL, fibrin, serum albumin, lens protein and renal glomerular basement membrane.

12. A method as claimed in claim 10 wherein the blood sugar levels of said patient are normal.

* * * * *